United States Patent [19]
Yahiaoui et al.

[11] Patent Number: 6,017,832
[45] Date of Patent: Jan. 25, 2000

[54] METHOD AND COMPOSITION FOR TREATING SUBSTRATES FOR WETTABILITY

[75] Inventors: Ali Yahiaoui, Roswell; Gabriel H. Adam, Alpharetta, both of Ga.

[73] Assignee: Kimberly-Clark Worldwide, Inc., Neenah, Wis.

[21] Appl. No.: 08/994,828

[22] Filed: Dec. 19, 1997

Related U.S. Application Data

[63] Continuation-in-part of application No. 08/898,188, Jul. 22, 1997
[60] Provisional application No. 60/025,621, Sep. 4, 1996.
[51] Int. Cl.⁷ .................... D06M 13/165; D06M 15/03; D06M 15/643
[52] U.S. Cl. .................. 442/118; 106/217.9; 106/244; 106/287.13; 106/287.16; 252/8.61; 442/170; 442/400; 442/401; 524/58; 524/837
[58] Field of Search ................................... 442/118, 170, 442/400, 401; 106/217.9, 244, 287.13, 287.16; 252/8.61; 524/58, 837

[56] References Cited

U.S. PATENT DOCUMENTS

| | | |
|---|---|---|
| 3,338,992 | 8/1967 | Kinney . |
| 3,341,394 | 9/1967 | Kinney . |
| 3,502,538 | 3/1970 | Petersen . |
| 3,502,763 | 3/1970 | Hartmann . |
| 3,542,615 | 11/1970 | Dobo et al. . |
| 3,598,865 | 8/1971 | Lew . |
| 3,692,618 | 9/1972 | Dorschner et al. . |
| 3,802,817 | 4/1974 | Matsuki et al. . |
| 3,844,865 | 10/1974 | Elton et al. . |
| 3,849,241 | 11/1974 | Butin et al. . |
| 3,855,046 | 12/1974 | Hansen et al. . |
| 3,891,008 | 6/1975 | D'Entremont . |
| 3,951,945 | 4/1976 | Heesen et al. . |
| 3,966,918 | 6/1976 | Kawamata et al. . |
| 4,041,203 | 8/1977 | Brock et al. . |
| 4,075,290 | 2/1978 | Denzel et al. . |
| 4,125,662 | 11/1978 | Weiner et al. . |
| 4,169,910 | 10/1979 | Graboski . |
| 4,275,120 | 6/1981 | Weiner . |
| 4,291,092 | 9/1981 | Weiner . |
| 4,297,408 | 10/1981 | Stead et al. . |
| 4,339,494 | 7/1982 | Weiner . |
| 4,340,563 | 7/1982 | Appel et al. . |
| 4,374,888 | 2/1983 | Bornslaeger . |
| 4,413,032 | 11/1983 | Hartmann et al. . |
| 4,460,644 | 7/1984 | Pavlich . |
| 4,627,931 | 12/1986 | Malik . |
| 4,672,091 | 6/1987 | Berta . |
| 4,753,844 | 6/1988 | Jones et al. . |
| 4,764,505 | 8/1988 | Fujinuma et al. . |
| 4,789,588 | 12/1988 | Suzuki et al. . |
| 4,791,144 | 12/1988 | Nagou et al. . |
| 4,878,974 | 11/1989 | Kagawa . |
| 4,895,622 | 1/1990 | Barnett et al. . |
| 4,959,396 | 9/1990 | Yankov et al. . |
| 4,975,469 | 12/1990 | Jacoby et al. . |
| 4,995,884 | 2/1991 | Ross et al. . |
| 5,045,387 | 9/1991 | Schmalz . |
| 5,057,361 | 10/1991 | Sayovitz et al. . |
| 5,108,820 | 4/1992 | Kaneko et al. . |
| 5,108,827 | 4/1992 | Gessner . |
| 5,109,127 | 4/1992 | Sekiguchi et al. . |
| 5,154,855 | 10/1992 | Sekiguchi et al. . |
| 5,169,706 | 12/1992 | Collier, IV et al. . |
| 5,169,712 | 12/1992 | Tapp . |
| 5,176,953 | 1/1993 | Jacoby et al. . |
| 5,190,747 | 3/1993 | Sekiguchi et al. . |
| 5,236,963 | 8/1993 | Jacoby et al. . |
| 5,238,586 | 8/1993 | Uphues et al. . |
| 5,258,221 | 11/1993 | Meirowitz et al. . |
| 5,266,392 | 11/1993 | Land et al. . |
| 5,268,126 | 12/1993 | Balzer ................................. 252/312 |
| 5,272,326 | 12/1993 | Fujita et al. . |
| 5,310,730 | 5/1994 | Fujinuma et al. . |
| 5,317,035 | 5/1994 | Jacoby et al. . |
| 5,322,728 | 6/1994 | Davey et al. . |
| 5,336,552 | 8/1994 | Strack et al. . |
| 5,342,534 | 8/1994 | Skrobala et al. . |
| 5,362,497 | 11/1994 | Yamada et al. . |
| 5,373,044 | 12/1994 | Adams et al. . |

(List continued on next page.)

FOREIGN PATENT DOCUMENTS

| | | |
|---|---|---|
| 598 204 | 5/1994 | European Pat. Off. . |
| 0712892 | 5/1996 | European Pat. Off. . |
| 41 36 540 | 5/1992 | Germany .................... A61F 13/15 |
| 4131551 | 3/1993 | Germany . |
| 19600467 | 7/1997 | Germany . |
| 01 104700 | 4/1989 | Japan ........................... A61K 7/00 |
| 95/27005 | 10/1995 | WIPO . |
| 97/15651 | 5/1997 | WIPO . |
| 98/10134 | 3/1998 | WIPO . |

OTHER PUBLICATIONS

Chemical Abstract No. 124:185108, abstract of an article by Foerster et al., entitled *Physicochemical properties of alkyl polyglycosides in personal care products*, Parfuem. Kosmet. (1995), 76 (12). (No Month).

Manson, John A. and Sperling, Leslie H., *Polymer Blends & Composites*, Plenum Press, a division of Plenum Publishing Corp., New York, New York, pp. 273–277 (1976). (no month).

Rodgers, J.E., *Wide Line Nuclear Magnetic Resonance in Measurements of Finish–on–Fiber of Textile Products*, Spectroscopy, 9 (8), 40 (1994). (no month).

ICI Americas Inc. Technical Bulletin, *Ahcovel Base N–62 Liquid Nonionic Textile Softener*,1978. (no month).

*Primary Examiner*—Blaine Copenheaver
*Attorney, Agent, or Firm*—Pauley Petersen Kinne & Fejer

[57] ABSTRACT

A surfactant composition useful for imparting durability and wettability to a substrate includes first and second surfactants in combination. The first surfactant includes a compound selected from ethoxylated hydrogenated fatty oils, monosaccharides, monosaccharide derivatives, polysaccharides, polysaccharide derivatives, and combinations thereof. The second surfactant includes an organosilicon compound. The surfactant composition can be applied as an aqueous emulsion to a substrate such as a nonwoven web, to provide enhanced wettability after repeated washing cycles.

36 Claims, 4 Drawing Sheets

U.S. PATENT DOCUMENTS

| | | |
|---|---|---|
| 5,382,400 | 1/1995 | Pike et al. . |
| 5,397,507 | 3/1995 | Bauer et al. ............................ 252/549 |
| 5,446,100 | 8/1995 | Durrance et al. . |
| 5,456,982 | 10/1995 | Hansen et al. . |
| 5,468,797 | 11/1995 | Adams et al. . |
| 5,474,776 | 12/1995 | Koyanagi et al. . |
| 5,501,813 | 3/1996 | Fiischer et al. . |
| 5,540,979 | 7/1996 | Yahiaoui et al. . |
| 5,550,189 | 8/1996 | Qin et al. . |
| 5,562,848 | 10/1996 | Wofford et al. ......................... 252/8.84 |
| 5,567,808 | 10/1996 | Desai et al. . |
| 5,571,619 | 11/1996 | McAlpin et al. . |
| 5,582,904 | 12/1996 | Harrington . |
| 5,594,070 | 1/1997 | Jacoby et al. . |
| 5,605,651 | 2/1997 | Balzer ..................................... 252/312 |
| 5,605,683 | 2/1997 | Desai et al. . |
| 5,652,048 | 7/1997 | Haynes et al. . |
| 5,700,331 | 12/1997 | Thomas et al. .......................... 134/29 |

METHOD AND COMPOSITION FOR TREATING SUBSTRATES FOR WETTABILITY

This application is a continuation-in-part of U.S. patent application 08/898,188, filed Jul. 22, 1997, now allowed, the disclosure of which is incorporated herein by reference. The parent application claims priority from U.S. Provisional Application No. 60/025,621, filed Sep. 4, 1996.

BACKGROUND OF THE INVENTION

Nonwoven fabrics and their manufacture have been the subject of extensive development resulting in a wide variety of materials for numerous applications. For example, nonwovens of light basis weight and open structure are used in personal care items such as disposable diapers as liner fabrics that provide dry skin contact but readily transmit fluids to more absorbent materials which may also be nonwovens of a different composition and/or structure. Nonwovens of heavier weights may be designed with pore structures making them suitable for filtration, absorbent and barrier applications such as wrappers for items to be sterilized, wipers or protective garments for medical, veterinary or industrial uses. Even heavier weight nonwovens have been developed for recreational, agricultural and construction uses. These are but a few of the practically limitless examples of types of nonwovens and their uses that will be known to those skilled in the art who will also recognize that new nonwovens and uses are constantly being identified. There have also been developed different ways and equipment to make nonwovens having desired structures and compositions suitable for these uses. Examples of such processes include spunbonding, meltblowing, carding, and others which will be described in greater detail below. The present invention has general applicability to nonwovens as will be apparent to one skilled in the art, and it is not to be limited by reference or examples relating to specific nonwovens which are merely illustrative.

It is not always possible to efficiently produce a nonwoven having all the desired properties as formed, and it is frequently necessary to treat the nonwoven to improve or alter properties such as wettability by one or more fluids, repellency to one or more fluids, electrostatic characteristics, conductivity, and softness, to name just a few examples. Conventional treatments involve steps such as dipping the nonwoven in a treatment bath, coating or spraying the nonwoven with the treatment composition, and printing the nonwoven with the treatment composition. For cost and other reasons it is usually desired to use the minimum amount of treatment composition that will produce the desired effect with an acceptable degree of uniformity. It is known, for example, that the heat of an additional drying step to remove water applied with the treatment composition can deleteriously affect strength properties of the nonwoven as well as add cost to the process. It is, therefore, desired to provide an improved treatment process and/or composition for nonwovens that can efficiently and effectively apply the desired treatment without adversely affecting desirable nonwoven web physical properties and achieve the desired results.

It is also known that most conventional surfactants that are water dispersible are not prone to form high-solids (>10 weight %), low viscosity (<100 cp), stable mixtures with water. An additional desire, therefore, is to provide a high-solids treatment bath that is stable without phase separation over an extended period and that exhibits a low viscosity profile at room temperature as well as means to effectively apply the surfactant treatment to impart a durable hydrophilic character to the substrate such as a nonwoven.

SUMMARY OF THE INVENTION

The present invention is directed to an improved composition and method for effectively and efficiently treating nonwovens to impart one or more desired property such as durable wettability and to the resulting improved nonwovens. The process and composition include at least one surfactant in combination with a viscosity modifier and includes subjecting one or both sides of the nonwoven to a neat or high solids treating composition. Drying and its deleterious effects are essentially or completely unnecessary, and the process provides means to uniformly treat one or both sides of the nonwoven to a desired degree without adversely affecting the durability of the result, for example web wettability. In accordance with the process of the invention, a nonwoven fabric is directed to a treating station where a treating composition that is preferably less than about 90% solvent is applied to the fabric by means of coating, dipping, spraying, or the like, in an amount to effectively treat the area of the fabric contacted by the composition. The treated fabric may then be subjected to a similar treatment on the same or the opposite side and minimal drying, if necessary. Moreover, the process of the invention greatly facilitates any cleanup steps that may be required. The resulting treated nonwovens have been shown to be uniformly, durably and effectively treated with reduced composition requirements and minimal or no adverse effects. Preferred treatments include a combination of a surfactant which, itself, is a blend of ethoxylated hydrogenated castor oil and sorbitan monooleate, and a viscosity modifier, an alkyl polyglycoside. These treatments for nonwovens are of particular use for personal care, medical and other applications such as wipers, protective garments, applicators, and others where compositions are applied to a substrate desirably at high solids.

The present invention is also directed to a composition and method for treating nonwovens to impart relatively high rewet (durability) performance for accepting multiple fluid insults and fast fluid intake rates. For this application, the preferred treatments include a combination including at least two surfactants. A first surfactant includes a compound selected from an ethoxylated hydrogenated fatty oil, a monosaccharide, a monosaccharide derivative, a polysaccharide, a polysaccharide derivative and combinations thereof. A second surfactant includes an organosilicon compound. The surfactant combination can be prepared in the form of an aqueous emulsion which is then homogenized. In this embodiment, the second surfactant acts as a powerful emulsifier, flow/viscosity modifier and leveling aid. Nonwovens treated in this fashion are especially useful for diapers, training pants, incontinence garments, and other applications requiring possible exposure to multiple fluid insults.

The foregoing and other features and advantages of the invention will become further apparent from the following detailed description of the presently preferred embodiments, read in conjunction with the examples and drawings. The detailed description, examples and drawings are merely illustrative rather than limiting, the scope of the invention being defined by the appended claims and equivalents thereof.

DETAILED DESCRIPTION OF THE INVENTION

Definitions

Figure 1:
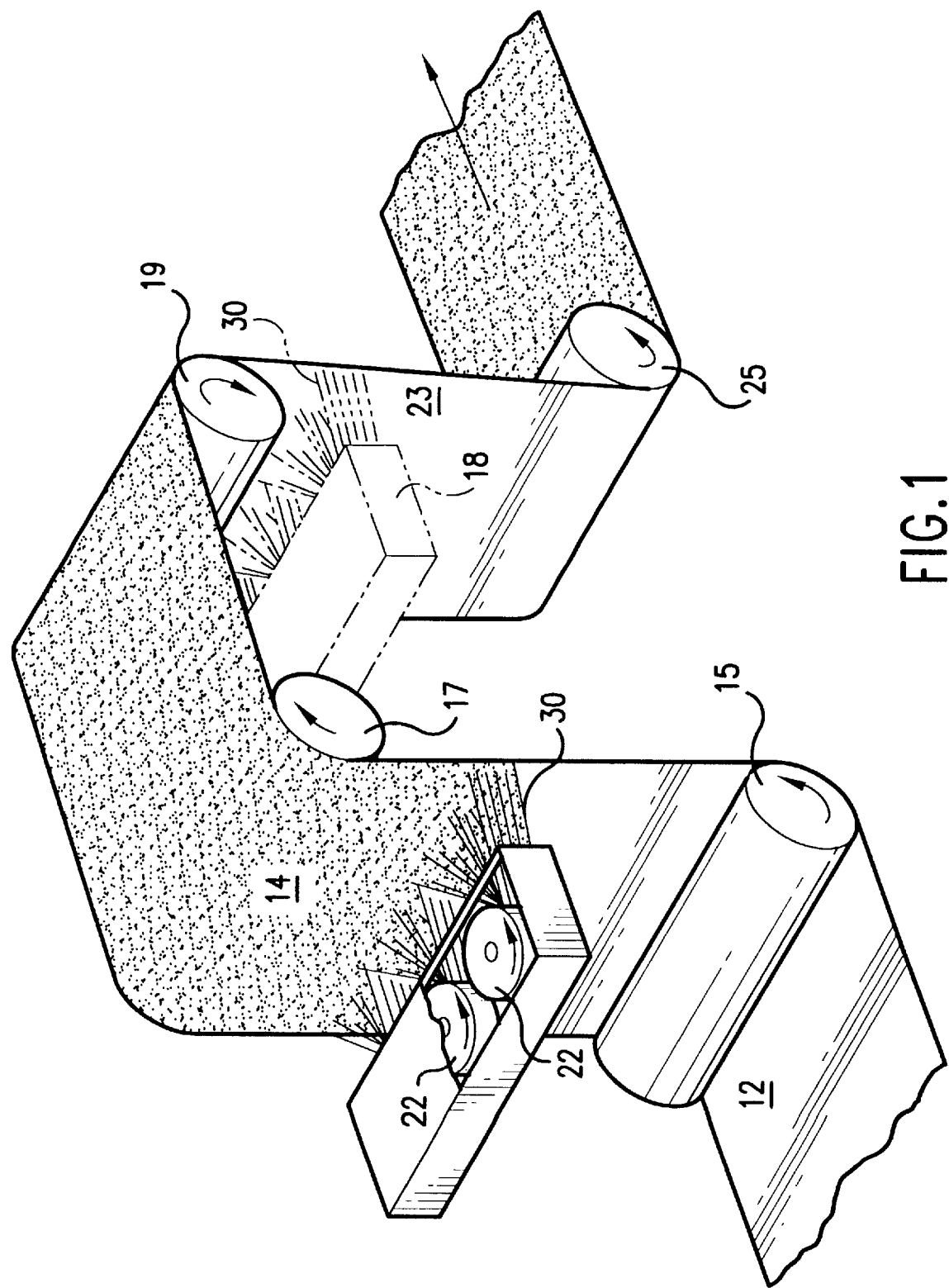
FIG. 1 is a schematic illustration of a treating process of the present invention useful for application to one or both sides of a nonwoven web substrate.

As used herein the term "nonwoven fabric or web" means a web having a structure of individual fibers or threads which are interlaid, but not in a regular or identifiable manner as in a knitted fabric. It also includes foams and films that have been fibrillated, apertured or otherwise treated to impart fabric-like properties. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Levy, and U.S. Pat. No. 3,542,615 to Dobo et al. Spunbond fibers are quenched and generally not tacky when they are deposited onto a collecting surface. Spunbond fibers are generally continuous and have average diameters larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin. Meltblown fibers are microfibers which may be continuous or discontinuous, are generally smaller than 10 microns in average diameter, and are generally tacky when deposited onto a collecting surface.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic, atactic and random symmetries.

As used herein, the term "machine direction" or MD means the length of a fabric in the direction in which it is produced. The term "cross machine direction" or CD means the width of fabric, i.e. a direction generally perpendicular to the MD.

As used herein the term "monocomponent" fiber refers to a fiber formed from one or more extruders using only one polymer. This is not meant to exclude fibers formed from one polymer to which small amounts of additives have been added for color, anti-static properties, lubrication, hydrophilicity, etc. These additives, e.g. titanium dioxide for color, are generally present in an amount less than 5 weight percent and more typically about 2 weight percent.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

As used herein the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein the term "blend" as applied to polymers, means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, through air bonding or "TAB" means a process of bonding a nonwoven, for example, a bicomponent fiber web in which air which is sufficiently hot to melt one of the polymers of which the fibers of the web are made is forced through the web. The air velocity is often between 100 and 500 feet per minute and the dwell time may be as long as 6 seconds. The melting and resolidification of the polymer provides the bonding. Through air bonding has restricted variability and is generally regarded a second step bonding process. Since TAB requires the melting of at least one component to accomplish bonding, it is restricted to webs with two components such as bicomponent fiber webs or webs containing an adhesive fiber or powder.

As used herein "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds and a wire weave pattern looking as the name suggests, e.g. like a window screen. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

As used herein, the term "personal care product" means diapers, training pants, absorbent underpants, adult incontinence products, and feminine hygiene products.

As used herein, the term "durable wettability" or "durably wettable" means the ability to withstand at least two and, advantageously at least 3, insults using the runoff test described below.

As used herein, the term "hydrophilic" means that the polymeric material has a surface free energy such that the polymeric material is wettable by an aqueous medium, i.e. a liquid medium of which water is a major component. That is, an aqueous medium wets the nonwoven fabric that has been treated from a surfactant bath. The surfactant bath is made from at least 10% by weight of surfactant or surfactant mixtures and of no than about 90% solvent such as water, for example.

TEST METHODS

The run-off test (exposure) and wash/dry procedure are described in U.S. Pat. No. 5,258,221 to Meirowitz et al. which is incorporated herein in its entirety by reference. Typically, a generally rectangular, 8-inch by 15 inch (about 20-cm by 38-cm) sample of a fibrous web, such as a nonwoven web, is mounted on top of an absorbent core composed of polypropylene, wood pulp fibers, and/or a superabsorbent material. The resulting test assembly is centered on the inclined surface and held in place with tape at each corner of the assembly. The angle of the inclined surface is 45° instead of the 30° angle described in the patent. The funnel is located at approximately 7.8 inches (about 200 mm) from the bottom or lower edge of the test assembly. The valve of the funnel is located approximately 10 mm above the top surface of the test assembly. One hundred ml of water having a temperature of 35° C. is placed in the funnel. The valve of the funnel is opened to dispense the water over a period of about 15 seconds. The amount of water (grams) which runs off and is collected in the collection means is determined and recorded. A fibrous web is typically considered to pass the modified run-off test if the amount of water collected in the collection means is less than an amount deemed appropriate for a given type of fibrous web. For example, when the fibrous web is a lightweight (e.g. having a basis weight of 0.6 ounces per square yard or about 20 grams per square meter) spunbonded nonwoven web, the amount of water collected should be less than 20 ml.

The wash/dry cycle was modified by utilizing 500 ml, rather than one liter, of room temperature water (about 23° C.). Thus, the generally rectangular sample of coated porous substrate described above was placed in the 500 ml of water. The sample was allowed to remain in the water for one minute while being agitated at 15–20 revolutions per minute by a mechanical shaker. The sample was removed from the water and excess liquid squeezed back into the wash water container. The sample was allowed to dry in air overnight or was dried in an oven (Blue M Model OV-475A-3 from General Signal, Blue Island, Ill.) at 80° C. for 20 minutes and then was subjected to the modified run-off test described above. This process was repeated the desired number of times.

The strip tensile test is a measure of breaking strength and elongation or strain of a fabric when subjected to unidirectional stress. This test is a modified version of ASTM Standard Test Method D882 (Test Method for Tensile Properties of Thin Plastic Sheeting).

To measure peak strength for the purposes of the present invention, the following modifications are made to the standard procedure:

The rate of separation imparted to the grip members of the testing apparatus is kept at a rate of 50 mm/minutes for all samples.

The initial separation between the grip members is varied from 1 inch to 3 inches depending on the type of sample tested. The initial separation when testing tape backing materials is 1.5 inches, and the initial separation when testing outer cover materials and securement zone materials is 3 inches.

The peak strength is calculated by dividing the maximum load on the load-crosshead travel curve by the width of the sample.

The results are expressed in pounds to break and percent stretch before breakage. Higher numbers indicate a stronger, more stretchable fabric. The term "load" means the maximum load or force, expressed in units of weight, required to break or rupture the specimen in a tensile test. The term "strain" or "total energy" means the total energy under a load versus elongation curve as expressed in weight-length units. The term "elongation" means the increase in length of a specimen during a tensile test. Values for grab tensile strength and grab elongation are obtained using a specified width of fabric, usually 4 inches (102 mm), clamp width and a constant rate of extension. The sample is wider than the clamp to give results representative of effective strength of fibers in the clamped width combined with additional strength contributed by adjacent fibers in the fabric. The specimen is clamped in, for example, an Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154, which have 3 inch (76 mm) long parallel clamps. This closely simulates fabric stress conditions in actual use.

Liquid strike-through time: This test is identified as EDANA 150.1-90 and measures the time taken for a known volume of liquid (simulated urine) applied to the surface of a nonwoven test sample in contact with an underlying absorbent pad to pass through the nonwoven. In general, a 50 ml burette is positioned on a ring stand with the tip inside a funnel. A standard absorbent pad of 5 plies of specified filter paper (482% absorbency) is placed on an acrylic glass base plate below the funnel, and a nonwoven sample is placed on top of the absorbent. An acrylic glass strike-through plate 25 mm thick and weighing 500 g is placed over the sample with the cavity centered 5 mm below the funnel. The burette is filled with liquid, keeping the funnel closed, and a quantity of the liquid (e.g., 5 ml or 10 ml) is run into the funnel. The 5 ml or 10 ml is allowed to discharge starting a timer which stops when the liquid has penetrated into the pad and fallen below a set of electrodes, and the elapsed time is recorded. For the Examples below, this test was repeated 5 times for each sample using the same test pieces each repetition, and the times were averaged. Examples 1–80 were tested using 10 ml of the liquid. Examples 81–88 were tested using 5 ml of the liquid. The liquid used was Blood Bank Saline, available from Stephens Scientific Co., Catalog No. 8504.

It is also possible to have other materials blended with the polymer used to produce a nonwoven according to this invention like fire retardants for increased resistance to fire and/or pigments to give each layer the same or distinct colors. Also additives for scents, odor control, antibacterials, lubricants and the like may be used. Such components for spunbond and meltblown thermoplastic polymers are known in the art and are frequently internal additives. A pigment, if used, is generally present in an amount less than 5 weight percent of the layer while other materials may be present in a cumulative amount less than about 25 weight percent, for example.

The fibers from which the fabric of this invention is made may be produced, for example, by the meltblowing or spunbonding processes which are well known in the art. These processes generally use an extruder to supply melted thermoplastic polymer to a spinneret where the polymer is fiberized to yield fibers which may be staple length or longer. The fibers are then drawn, usually pneumatically, and deposited on a moving foraminous mat or belt to form the nonwoven fabric. The fibers produced in the spunbond and meltblown processes are microfibers as defined above.

The manufacture of meltblown webs is discussed generally above and in the references.

The fabric of this invention may be a multilayer laminate. An example of a multilayer laminate is an embodiment wherein some of the layers are spunbond and some meltblown such as a spunbond/meltblown/spunbond (SMS) laminate as disclosed in U.S. Pat. No. 4,041,203 to Brock et al., U.S. Pat. No. 5,169,706 to Collier, et al., U.S. Pat. No. 5,540,979 to Yahiaoui et al. and U.S. Pat. No. 4,374,888 to Bornslaeger. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy.

Spunbond nonwoven fabrics are generally bonded in some manner as they are produced in order to give them sufficient structural integrity to withstand the rigors of further processing into a finished product. Bonding can be accomplished in a number of ways such as hydroentanglement, needling, ultrasonic bonding, adhesive bonding, stitchbonding, through-air bonding and thermal bonding.

As alluded to above, an important parameter for treated nonwovens for many applications is durability of wettability or the ability to withstand multiple insults in use. For diaper liner applications, for example, the ability to maintain wettability properties after 3 or more insults is extremely desirable. Some available treatments such as a blend of ethoxylated hydrogenated castor oil and sorbitan monooleate (Ahcovel Base N-62 available from Hodgsen Chemical Co., manufactured by ICI (also referred to as simply "Ahcovel")) have been shown to be durable according to this standard.

The chemical formulas for these components are as follows:

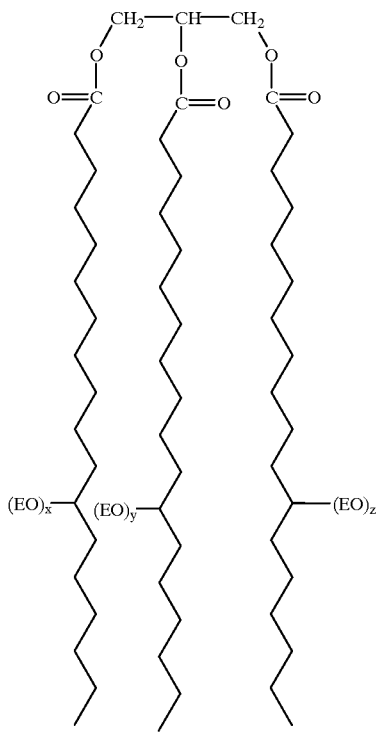

Ethoxylated Hydrogenated Castor Oil

+

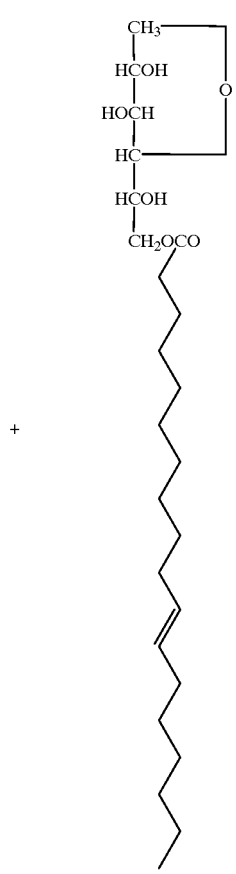

Sorbitan Monooleate

However, this treatment is very viscous and difficult to apply at high solids using conventional treating methods. Traditional viscosity modification additives or surfactant blends may reduce the viscosity of this treatment, but they adversely affect the durability of the treated fabric as is discussed below with reference to Tables 3 and 4. In accordance with the invention, it has been found that use of specific alkyl polyglycosides not only reduce the viscosity of this treatment but maintain the desirable durability. For best results the alkyl polyglycoside is one with 8 to 10 carbons in the alkyl chain (e.g. Glucopon 220UP) and is included in an amount of about 5% to about 80%, advantageously about 5% to about 10%, based on the total composition weight and the weight of the alkyl polyglycoside composition, which may be aqueous, containing about 40% water, for example.

Glucopon 220UP is an octylpolyglycoside having the following chemical formula:

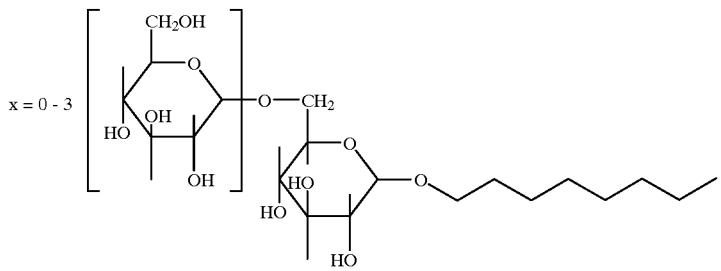

Table 1 below illustrates the effect on viscosity of Ahcovel Base N-62 of the addition of Glucopon 220UP a solution of 60% alkyl polyglycoside in 40% water by weight available from Henkel Corporation (also referred to as simply "Glucopon"). Viscosity determinations were made on 20% overall solids compositions and at a shear rate of 20 (1/sec) using a Viscometer: Brookfield DV II+, Spindle CP41 in each case.

TABLE 1

Effect of Glucopon on Viscosity* of Ahcovel at 20% Solids

| Treating Composition | Ratio | Viscosity (cp.) | Temp. (C.) | Shear Rate (sec.$^{-1}$) |
|---|---|---|---|---|
| Ahcovel | 1 | 1103 | 25 | 20 |
| Ahcovel | 1 | 150 | 47 | 20 |
| Ahcovel/Glucopon | 20/1 | 40 | 25 | 20 |
| Ahcovel/Glucopon | 15/1 | 14 | 25 | 20 |
| Ahcovel/Glucopon | 10/1 | <12.3 | 25 | 20 |
| Ahcovel/Glucopon | 5/1 | <12.3 | 25 | 20 |
| Ahcovel/Glucopon | 3/1 | <12.3 | 25 | 20 |
| Ahcovel/Glucopon | 1/1 | <12.3 | 25 | 20 |

*Measurements with Brookfield DVII + viscometer, spindle CP-41

For purposes of the invention, achieving a viscosity of less than about 100 cp under application conditions, preferably room temperature, is desirable so that high solids conventional application systems and procedures can be employed such as the WEKO Rotor Dampening System available from Weko. Others such as brush spray applicators and coating and printing applicators may be used as will be apparent to those skilled in the art. As shown above, the surfactant alone fails to meet this requirement, but as little as 1 part in 20 of the addition of an alkyl polyglycoside such as Glucopon 220UP reduces its viscosity dramatically.

The present invention is believed applicable to reduced viscosity treatment with a wide variety of compositions although the combination with surfactant compositions such as the Ahcovel series is highly preferred because of the durability of such treatments. Where this degree of durability is not critical, however, it is only essential that the composition contain effective amounts of the surfactant combination and the viscosity modifier to treat the nonwoven. To determine suitability, the composition may be tested by Brookfield viscosity. Preferred compositions are those that have a viscosity of about 2000 cps or less. Specific examples include Triton x-102, an alkylphenol ethoxylate surfactant available from Union Carbide, Y12488 and Y12734, series of ethyoxylated polydimethyl siloxanes available from OSI, Masil SF-19, an ethoxylated trisiloxane available from PPG, PEG 200, 400 and 600 series of polyethylene glycol monosterates, distearates, and monolaurates available from PPG, GEMTEX SM-33 and SC75 series, and dialkyl sulfosuccinates available from Finetex as well as water soluble polymers such as polyvinyl pyrrolidone, polyvinyl alcohol, ethyl hydroxyethyl cellulose, carboxymethyl cellulose, hydroxypropyl cellulose, starch, agar, and other natural water soluble polymers. Other surfactants include ethoxylated terephthalates such as Milease T from ICI, alcohol ethoxylates such as Mazawet 77 from PPG, and PEO-PPO block copolymers such as Pluronic L 101 from BASF. Examples of the viscosity modifier include Glucopon 220 or 225, both alkyl polyglycosides with 8–10 carbon atoms in the alkyl chain and available from Henkel Corporation. The resulting mixture will have a viscosity as an emulsion of less than 100 cp, preferably, and even more desirably, less than 50 cp under conditions of application.

In a preferred embodiment, a first surfactant includes a compound selected from the group consisting of an ethoxylated hydrogenated fatty oil, a monosaccharide, a monosaccharide derivative, a polysaccharide, a polysaccharide derivative, and combinations thereof. The first surfactant is combined with a second surfactant which includes an organosilicon compound. The first surfactant may include a blend of ethoxylated hydrogenated castor oil and sorbitan monooleate, and may be combined with a second surfactant including an alkoxylated polysiloxane. For instance, Ahcovel Base N-62 which is a blend of an ethoxylated hydrogenated fatty oil and a monosaccharide derivative, may be combined with Masil SF-19. Masil SF-19 is an alkoxylated polysiloxane having the following chemical formula:

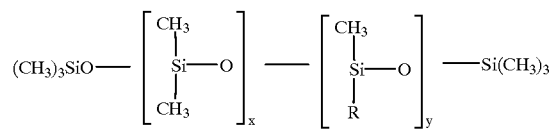

where R is defined as:

($R^1$=H or alkyl)
and X, Y, P and Q are positive integers.

The first and second surfactants may be initially prepared in the form of an aqueous emulsion. The aqueous emulsion may include about 1–60% by weight total surfactant solids and about 40–99% by weight water. Desirably, the aqueous emulsion may include about 10–40% by weight total surfactant solids and about 60–90% by weight water. More suitably, the aqueous emulsion may contain about 15–35% by weight total surfactant solids and about 65–85% by weight water. The surfactant combination may be dispersed in the water in the form of small droplets or microdroplets using vigorous agitation or other suitable mixing/emulsification process known to persons skilled in the art.

The emulsion may be then homogenized by mixing at an elevated temperature of about 130° F. or greater. When the emulsion is homogenized, the aqueous system including the first and second surfactants exhibits a much lower viscosity than a similarly prepared system which contains the first surfactant without the second surfactant. The second surfactant, which preferably is present at low levels relative to the first surfactant, acts as a powerful emulsifier, flow/viscosity modifier, and leveling agent.

The combination of first and second surfactants should include, on a dry weight basis, about 50–99.5 parts by weight first surfactant and about 0.5–50 parts by weight second surfactant. Desirably, the combination includes about 65–95 parts by weight first surfactant and about 5–35 parts by weight second surfactant. Preferably, the combination should include about 70–85 parts by weight first surfactant and about 15–30 parts by weight second surfactant.

The foregoing combination of first and second surfactants is particularly useful for applications requiring high rewet (durability) performance, which involve exposure to multiple fluid insults and/or a fast fluid intake rate. The advantages of this surfactant blend further include excellent processability (i.e., low viscosity) at a relatively high solids content in water, and excellent processability at high temperatures (e.g., 130° F. or higher) which inhibit bacterial growth without the addition of chemical preservatives. Also, efficient wet-out of the nonwoven fabric results from uniform treatment of the nonwoven fabric at fairly low levels.

For instance, the fabric may be effectively treated with the surfactant combination at levels below about 2.0% by weight dry surfactant solids relative to the basis weight of the fabric, such as, for instance, levels of about 0.1–1.5% by weight relative to the basis weight of the fabric. Desirably, the fabric is treated at levels of about 0.1–1.0% by weight surfactant solids relative to the basis weight of the fabric. Preferably, the fabric is treated at levels of about 0.1–0.5% by weight surfactant solids relative to the basis weight of the fabric.

Another advantage of using the combination of first and second surfactants is that there is an apparent synergy between the durable (rewet) character of the first surfactant and the emulsification power and surface activity of the second surfactant. This synergy causes the nonwoven web to have significantly improved fluid handling properties, including improved rewet and fluid intake rate.

Although the present invention is suitable for treating nonwovens broadly, it is most effective, and therefore preferred, for nonwovens having properties that lend them to high speed, efficient treatment. These properties include basis weight, for example, 5 to 500 gsm, thickness, for example 0.2 to 10 millimeters, and the like.

In order to maximize the advantages of the present invention, the selection of the nonwoven and the treatment composition are preferably made so that the composition may be applied with no more than about 80%, and preferably less water.

Referring to FIG. 1, a process will be described for application to one or both sides of a traveling web. It will be appreciated by those skilled in the art that the invention is equally applicable to inline treatment or a separate, offline treatment step. Web 12, for example a spunbond or meltblown nonwoven is directed under support roll 15, to a treating station including rotary spray heads 22 for application to one side 14 of web 12. An optional treating station 18 (shown in phantom) which may include rotary spray heads (not shown) can also be used to apply to opposite side 23 of web 12 directed over support rolls 17,19. Each treatment station receives a supply of treating liquid 30 from a reservoir (not shown). The treated web may then be dried if needed by passing over dryer cans (not shown) or other drying means and then under support roll 25 to be wound as a roll or converted to the use for which it is intended. Alternative drying means include ovens, through air dryers, infra red dryers, air blowers, and the like.

Figure 2:
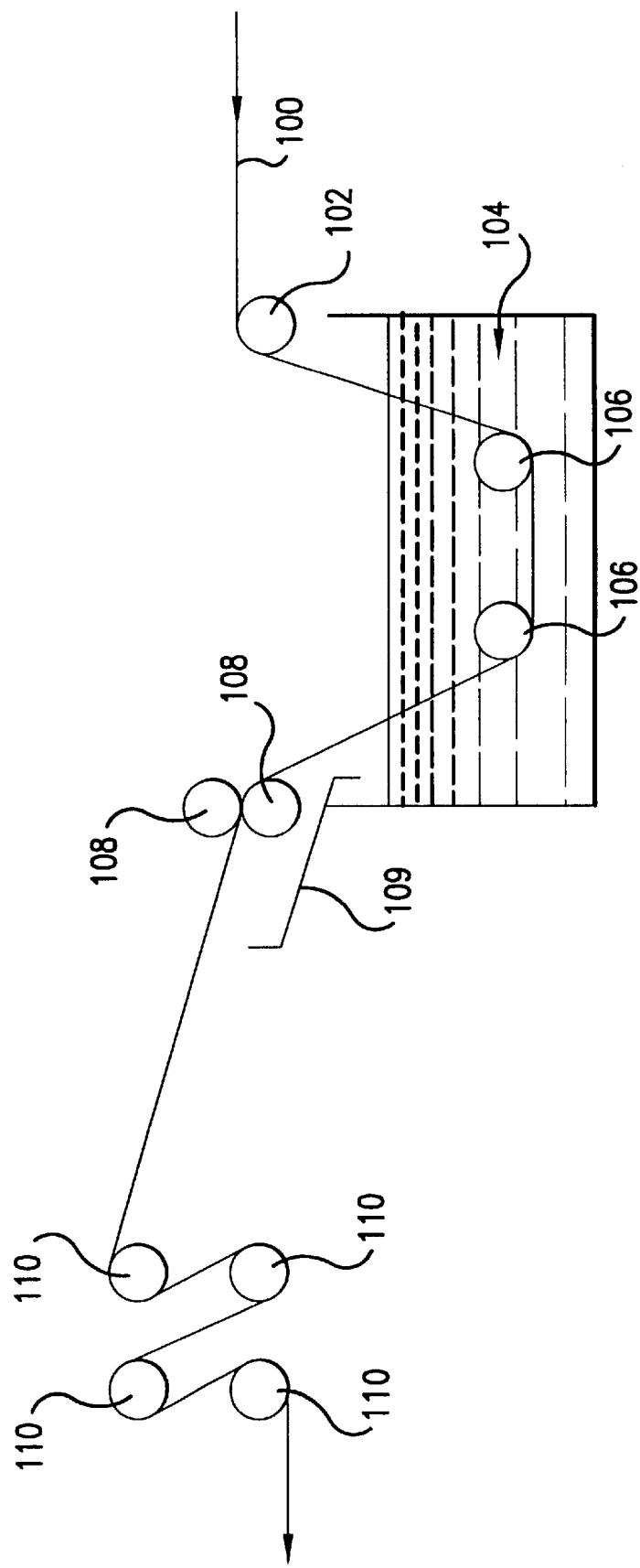
FIG. 2 is a similar schematic illustration showing an alternative treating system.

FIG. 2 illustrates an alternative arrangement using a dip and squeeze application step. As shown, web 100 passes over guide roll 102 and into bath 104 with the treatment time controlled by guide rolls 106. The nip between squeeze rolls 108 removes excess treating composition which is returned to the bath by catch pan 109. Drying cans 110 remove remaining moisture.

It is also understood that the method and hydrophilic surface treatment of nonwoven materials with topical application of surfactants of this invention may incorporate not only multiple surfactants for improved wettability with aqueous fluids (e.g. urine), or facilitates management of other body fluids (blood, menstrual fluid, feces, etc.), but may also be used to incorporate bioactive compounds and macromolecules, which may afford biofunctional attributes to the surface treatments of this invention (e.g. antibacterial activity, preservatives, anti-inflammatory, odor control, skin wellness and the like).

The present invention is further illustrated by the following examples which are representative of the invention although other examples will be apparent to those skilled in the art and are intended to be covered by the claims.

EXAMPLES

Examples 1–43

High Solids/Low Viscosity Surfactant Formulations

Numerous methods for hydrophilic treatment of nonwoven materials with surfactants from baths at low-solids content are known and are commonly used. However, because of the high solvent content, as a drying step is required . It is known that the heat effects of the drying process negatively impact the mechanical properties of nonwoven materials following their surface treatment (Table 2). Thus, employing a high-solids bath minimizes or alleviates the need for drying requirement, thereby retaining the inherent tensile strength of the fabric. Other obvious advantages of a high-solids treatment system include: lower cost for surfactant formulation, shipping and storage, conserved energy and lower treatment cost, and better treatment uniformity. As used herein, "high solids" means a concentration of at least about 10% solids, and advantageously, such compositions are at least about 20% solids.

TABLE 2

Comparative data on the effect of drying on mechanical properties of 0.6 osy polypropylene spunbond fabrics.

|  | Strip Tensile Peak Energy CD Dry | Strip Tensile Peak Load CD Dry | Strip Tensile Peak Strain CD Dry, % | Strip Tensile Peak Energy MD Dry | Strip Tensile Peak Load MD Dry | Strip Tensile Peak Strain MD Dry, % |
|---|---|---|---|---|---|---|
| Fabric 1* | 7.62 | 7.90 | 50.66 | 10.08 | 12.42 | 39.44 |
| Fabric 2** | 5.06 | 6.24 | 52.45 | 6.19 | 11.42 | 27.61 |

*Fabric 1: treated with 0.9% Ahcovel/Glucopon with the high-solids WEKO process, where no drying is applied
**Fabric 2: treated with 0.9% Ahcovel/Glucopon with the low-solids saturation process, where drying at 220 F is applied On the other hand, surfactant treatment compositions at higher-solids content, also have presented drawbacks such as poor rheology, emulsion instability, gelling, and treatment variability. Other challenges related to topical application of surfactant for treatment of nonwoven materials, include durability or ability to maintain water wettability performance upon multiple exposures to aqueous fluids.

Then, the aim of this invention is three-fold: 1) to provide as a low viscosity/high-solids treatment compositions applicable at room temperature, 2) to provide high-solids treatment compositions with none or minimum drying requirements, 3) to provide treatment compositions that impart a durable wettability to nonwoven fabrics.

The following procedure is typical of the general method employed when utilizing the high solids/low viscosity treating compositions of the present invention.

Nonwoven fabric Typically, 14" wide rolls of 0.6 ounce per square yard (osy) spunbond fabric made of polypropylene fibers (ca. 2.2 dpf).

Surfactant formulation Typically, an aqueous treatment bath is prepared containing at least 0.075% antifoam (Dow 2210 from Dow Corning) and 20% by weight surfactant formulation (Table 3). After thorough mixing at room temperature, the surfactant formulation is poured into the treater tank where mixing is continued at room temperature, unless otherwise indicated (Table 3).

TABLE 3

Experimental data and comparison of durability of various hydrophilic treatments of nonwovens (High-solids WEKO process).

Treating Composition at 20% solids

| Example # | Code | Surfactant system | Ratio | Viscosity (cp) @ 20 sec$^{-1}$ 25 C | 47 C | Application Temp. (C) | Add-On (Wt %) | Durability (# cycles) |
|---|---|---|---|---|---|---|---|---|
| 1 | C1 | Ahcovel/Glucopon | 10:1 | <12 | | 25 | 0.3 | 2 |
| 2 | C2 | Ahcovel/Glucopon | 10:1 | <12 | | 25 | 0.6 | 4 |
| 3 | C3 | Ahcovel/Glucopon | 10:1 | <12 | | 25 | 0.9 | 6 |
| 4 | C4 | Ahcovel/Glucopon | 15:1 | 14 | | 25 | 0.3 | 2 |
| 5 | C5 | Ahcovel/Glucopon | 15:1 | 14 | | 25 | 0.5 | 4 |
| 6 | C6 | Ahcovel/Glucopon | 15:1 | 14 | | 25 | 0.9 | 8 |
| 7 | C7 | Ahcovel/Glucopon | 20:1 | 40 | | 25 | 0.3 | 3 |
| 8 | C8 | Ahcovel/Glucopon | 20:1 | 40 | | 25 | 0.5 | 6 |
| 9 | C9 | Ahcovel/Glucopon | 20:1 | 40 | | 25 | 0.9 | >10 |
| 10 | D1 | Ahcovel/Glucopon/SF 19 | 20:1:1 | 80 | | 25 | 0.3 | 1 |
| 11 | D2 | Ahcovel/Glucopon/SF 19 | 20:1:1 | 80 | | 25 | 0.6 | 2 |
| 12 | D3 | Ahcovel/Glucopon/SF 19 | 20:1:1 | 80 | | 25 | 0.9 | 4 |
| 13 | D4 | Ahcovel/Glucopon/SF 19 | 10:1:1 | 28 | | 25 | 0.6 | 0 |
| 14 | D5 | Ahcovel/Glucopon/SF 19 | 10:1:1 | 28 | | 25 | 0.6 | 0 |
| 15 | D6 | Ahcovel/Glucopon/SF 19 | 10:1:1 | 28 | | 25 | 0.9 | 1 |
| 18 | D9 | Ahcovel/Glucopon/SF 19 | 10:1:2 | 25 | | 25 | 0.9 | 0 |
| 19 | E1 | Ahcovel/Glucopon/Y 12488 | 10:1:1 | 28 | | 25 | 033 | 1 |
| 20 | E2 | Ahcovel/Glucopon/Y 12488 | 10:1:1 | 28 | | 25 | 0.6 | 2 |
| 21 | E3 | Ahcovel/Glucopon/Y 12488 | 10:1:1 | 28 | | 25 | 0.9 | 2 |
| 22 | E4 | Ahcovel/Glucopon/Y 12488 | 20:1:1 | 85 | | 25 | 0.6 | 1 |
| 23 | E5 | Ahcovel/Glucopon/Y 12488 | 20:1:1 | 85 | | 25 | 0.6 | 3 |
| 24 | E6 | Ahcovel/Glucopon/Y 12488 | 20:1:1 | 85 | | 25 | 0.9 | 6 |
| 25 | E7 | Ahcovel/Glucopon/Y 12488 | 10:1:2 | 35 | | 25 | 0.3 | 1 |
| 26 | E8 | Ahcovel/Glucopon/Y 12488 | 10:1:2 | 35 | | 25 | 0.6 | 1 |
| 27 | E9 | Ahcovel/Glucopon/Y 12488 | 10:1:2 | 35 | | 25 | 0.9 | 2 |
| 28 | A1 | Ahcovel | 1 | 1103 | 150 | 47 | 0.3 | 2 |
| 29 | A2 | Ahcovel | 1 | 1103 | 150 | 47 | 0.6 | 4 |
| 30 | A1 | Ahcovel | 1 | 1103 | 150 | 47 | 0.9 | >10 |
| 31 | B1 | Glucopon 220 UP | 1 | <12 | | 25 | 0.3 | 0 |
| 32 | B2 | Glucopon 220 UP | 1 | <12 | | 25 | 0.6 | 0 |
| 33 | B13 | Glucopon 220 UP | 1 | <12 | | 25 | 0.9 | 1 |
| 34 | G1 | Triton X-102 | 1 | 120 | 23 | 47 | 0.3 | 0 |
| 35 | G1 | Triton X-102 | 1 | 120 | 23 | 47 | 0.6 | 0 |
| 36 | G1 | Triton X-102 | 1 | 120 | 23 | 47 | 0.9 | 0 |
| 37 | H1 | PEG 400 ML | 1 | 40 | | 25 | 0.3 | 0 |
| 38 | H1 | PEG 400 ML | 1 | 40 | | 25 | 0.6 | 0 |
| 39 | H1 | PEG 400 ML | 1 | 40 | | 25 | 0.9 | 1 |
| 40 | F1 | Ahcovel/TL 2119 | 15:1 | 650* | | n/a | n/a | n/a |
| 41 | F3 | Ahcovel/PEG 400 ML | 15:1 | 350* | | n/a | n/a | n/a |
| 42 | F4 | Ahcovel/Pluronic L 101 | 15:1 | >10,000* | | n/a | n/a | n/a |
| 43 | F5 | Ahcovel/Mazawet 77 | 15:1 | 420* | | n/a | n/a | n/a |

*Viscosity too high for high solids applications

Application Process High solids low viscosity surfactant treatment compositions of this invention have been applied using as a WEKO treater (WEKO, Biel AG, Switzerland). The general WEKO configuration is a centrifugal damping application system using a single or double rotocarrier as shown in FIG. 1. The surfactant formulation is pumped to the WEKO header through a gear pump where it is fed to the damping rotors through restrictor tubes. The pilot WEKO equipment used in this invention is equipped with 6 rotors which spin at a speed of about 4500 rpm. Under the effect of a centrifugal force generated by the spinning rotors, the chemical is dispensed to the nonwoven fabric in the form of small droplets.

Throughput (gram/minute) is controlled and adjusted with different diameter restrictor tubes, header pressure and bath parameters (temperature and viscosity). A finer throughput control can be achieved by adding optional needle valves to the outlet ports of the header.

Drying All fabrics treated in examples 1–43 did not require any drying.

Add-On Level The add-on level on the fabric was measured by low resolution solid state nuclear magnetic resonance (NMR) spectroscopy using a Brucker Minispec 120 Pulse NMR (Brucker Spectrospin, Canada, Ltd.). Additional information about this analytical technique can also be found in the following reference "Wide Line Nuclear Magnetic Resonance in Measurements of Finish-on-Fiber of Textile Products", J. E. Rodgers, Spectroscopy, 9(8), 40 (1994).

One preferred surfactant treating composition is described in examples 1 through 6. As shown in Table 3, the fabrics of Examples 1–6 were treated from a relatively very low viscosity high solids aqueous emulsion of Ahcovel and Glucopon at ratios ranging from 10:1 to 20:1. It is noteworthy to mention that the treated fabrics did not need any post drying following their surface treatment with the WEKO process. The unusual finding in examples 1–6 as compared to other treatment reported in Table 3, is the durability of the surfactant/viscosity modifier treatment as herein described. The uniqueness of the treatment composition resides in its simultaneous fulfillment of the following attributes: 1) high solids, low viscosity, stable aqueous emulsion applicable at room temperature; 2) no drying was required; 3) improved treatment durability as assessed by the run-off test herein described.

in performance as the fabrics are exposed to multiple fluid insults. For examples, the fluid intake time of Triton X-102 treated fabrics appear to deteriorate on cycle 4 and 5, the performance of Ahcovel and Ahcovel/Glucopon, Ahcovel/

TABLE 4

Experimental data and comparison of durability of various hydrophilic treatments of nonwovens using various surfactants and co-surfactant systems applied from low-solids baths (Low-solids saturation process).

| | | Treating Composition | | | | | |
|---|---|---|---|---|---|---|---|
| Example # | Code | Surfactant system | Ratio | % Solids in Bath | Application Temp. (C) | Add-On (Wt %) | Durability (# cycles) |
| 44 | E10 | Ahcovel/Glucopon | 3:1 | 0.3 | 25 | 0.3 | 2 |
| 45 | E10 | Ahcovel/Glucopon | 3:1 | 0.6 | 25 | 0.6 | 3 |
| 46 | E10 | Ahcovel/Glucopon | 3:1 | 0.9 | 25 | 0.9 | 6 |
| 47 | E11 | Ahcovel/TL 2119 | 3:1 | 0.3 | 25 | 0.3 | 0 |
| 48 | E11 | Ahcovel/TL 2119 | 3:1 | 0.6 | 25 | 0.6 | 0 |
| 49 | E11 | Ahcovel/TL 2119 | 3:1 | 0.6 | 25 | 0.9 | 0 |
| 50 | E12 | Ahcovel/PEG 400 ML | 3:1 | 0.3 | 25 | 0.3 | 0 |
| 51 | E12 | Ahcovel/PEG 400 ML | 3:1 | 0.6 | 25 | 0.6 | 0 |
| 52 | E12 | Ahcovel/PEG 400 ML | 3:1 | 0.6 | 25 | 0.9 | 0 |
| 53 | El3 | Ahcovel/Pluronic L 101 | 3:1 | 0.3 | 25 | 0.3 | 1 |
| 54 | E13 | Ahcovel/Pluronic L 101 | 3:1 | 0.6 | 25 | 0.6 | 1 |
| 55 | E13 | Ahcovel/Pluronic L 101 | 3:1 | 0.6 | 25 | 0.9 | 2 |
| 56 | E14 | Ahcovel/G 2109 | 3:1 | 0.3 | 25 | 0.3 | 0 |
| 57 | E14 | Ahcovel/G 2109 | 3:1 | 0.6 | 25 | 0.6 | 0 |
| 58 | E14 | Ahcovel/G 2109 | 3:1 | 0.6 | 25 | 0.9 | 1 |
| 59 | A4 | Ahcovel | 1 | 0.3 | 25 | 0.3 | 2 |
| 60 | A5 | Ahcovel | 1 | 0.6 | 25 | 0.6 | 4 |
| 61 | A6 | Ahcovel | 1 | 0.9 | 25 | 0.9 | >10 |
| 62 | H2 | PEG 400 ML | 1 | 0.3 | 25 | 0.3 | 0 |
| 63 | H2 | PEG 400 ML | 1 | 0.6 | 25 | 0.6 | 0 |
| 64 | H2 | PEG 400 ML | 1 | 0.6 | 25 | 0.9 | 1 |
| 65 | G3 | Pluronic L 101 | 1 | 0.3 | 25 | 0.3 | 0 |
| 66 | G3 | Pluronic L 101 | 1 | 0.6 | 25 | 0.6 | 1 |
| 67 | G3 | Pluronic L 101 | 1 | 0.6 | 25 | 0.9 | 1 |
| 68 | G4 | Mazawet 77 | 1 | 0.3 | 25 | 0.3 | 0 |
| 69 | G4 | Mazawet 77 | 1 | 0.6 | 25 | 0.6 | 0 |
| 70 | G4 | Mazawet 77 | 1 | 0.6 | 25 | 0.9 | 0 |
| 71 | G5 | G 2109 | 1 | 0.3 | 25 | 0.3 | 0 |
| 72 | G5 | G 2109 | 1 | 0.6 | 25 | 0.6 | 0 |
| 73 | G5 | G 2109 | 1 | 0.6 | 25 | 0.9 | 0 |
| 74 | G6 | G 1282 | 1 | 0.3 | 25 | 0.3 | 0 |
| 75 | G6 | G 1282 | 1 | 0.6 | 25 | 0.6 | 0 |
| 76 | G6 | G 1282 | 1 | 0.6 | 25 | 0.9 | 0 |

The run-off test provides clear evidence that durable treatments are achieved in examples 1–11 and examples 27–29 of Table 3, and examples 44–46, 59–61 of Table 4. The run-off test results suggest that Ahcovel type surfactant alone and only certain coformulations of that surfactant with other surfactants pass the durability test. The durability results (from the run-off test) also suggest that a direct correlation between add-on level and extent of durability (or number of run-off cycles) exists only with Ahcovel type surfactant and certain coformulations such as Ahcovel/Glucopon, Ahcovel/Glucopon/SF 19 and Ahcovel/Glucopon/Y 12488. Such correlation is virtually non-existing with other types of single surfactant treatments as well as with certain Ahcovel type coformulations such as Ahcovel/PEG 400 ML, Ahcovel/TL 2119, Ahcovel/G2109. In the latter coformulation, addition of a secondary surfactant to Ahcovel appears to be detrimental to treatment durability.

The EDANA fluid strikethrough data provides information on fluid intake rate of a treated fabric, but also provides information on treatment durability as the same fabric is exposed 5 times to 10 ml of saline. The data presented in Table 6, clearly show that while the initial fluid intake time is about the same of all treated fabrics, there is a difference Glucopon/SF 19 appear to be less affected by the 5 exposures to saline. Therefore, the EDANA Fluid strikethrough data is consistent with treatment durability and results are consistent with the run-off test results.

Examples 44–76

Low-Solids Saturation Process

The following procedure is typical of the general method employed when utilizing the low-solids saturation process of the present invention:

Typically, an aqueous treatment bath was prepared containing 0.15% antifoam (Dow 2210 from Dow Corning), 0.5% hexanol and a desired amount of surfactant or co-surfactant is added at conditions indicated in Table 4. After thorough mixing at room temperature, the surfactant formulation is poured into the tank of the treating station (FIG. 2). Typically 14' wide rolls of a 0.6 osy fabric made of polypropylene spunbond fibers (ca. 2.2 dpf) were treated with surface treatment compositions as shown in Table 4. The add-on level is determined by measuring the percent wet pick up (% WPU) after the fabric is saturated and nipped between two rubber rolls. The % WPU is gravimetrically determined and calculated using the following formula:

$$\%\text{WPU} = \frac{(Ww - Wd)}{Wd} \times 100$$

where, Ww and Wd are the wet and dry weights, respectively of an approximately 12"×12" piece of fabric. For example as a 100% WPU measured on a fabric treated from a 0.3% solids bath would imply that a 0.3% add-on level on the fabric is achieved. The add-on level is controlled predominantly by the chemical concentration in the bath, the line speed and the nip pressure (Table 5).

TABLE 5

Process Conditions for the Low-Solids Saturation Application System

| Bath Concentration (weight %) | WPU* % | Target Add-on (weight %) | Line Speed (ft/min) | Nip Pressure (psi) |
|---|---|---|---|---|
| 0.3 | 100 | 0.3 | 70 | 40 |
| 0.6 | 100 | 0.6 | 35 | 35 |
| 0.9 | 100 | 0.9 | 16 | 30 |

*±5%

After the targeted add-on level is verified the treated fabrics were run over a series of steam-heated cans for drying (FIG. 2). The treated and dried fabric was then bench-tested for durability (run-off/wash/dry test) and fluid intake rate (EDANA Fluid Strikethrough Time).

foams were then oven dried at 60° C. for 30 minutes. The fluid intake time of the treated foams was measured for one insult, using the EDANA fluid strikethrough test, herein described, and results are reported in Table 7.

TABLE 7

Comparison of Fluid Intake Rate of Polyolefin Foams

| Sample | Intake Time (sec)** |
|---|---|
| Untreated LC 31 Foam | * |
| Ahcovel/Glucopon-treated LC 31 Foam | 2.9 |
| Triton X-102 treated LC 31 Foam | 5.5 |
| Untreated LC 33 Foam | * |
| Ahcovel/Glucopon-treated LC 33 Foam | 108 |
| Triton X-102 treated LC 33 Foam | >200 |

*Substrate too hydrophobic, fluid did not penetrate, intake time could not be measured
**Fluid intake time was only measured for one insult Example 78

The same treatments described in example 77 were applied to a different metallocene polyolefin foam (OPCELL LC33 foam from Sentinel Products Corp.). The fluid intake rate was measured as described in example 77 and the results are presented in Table 7.

The present invention is further described by the examples which follow.

TABLE 6

Experimental Data and Comparison of EDANA Fluid Strikethrough Time of Various Hydrophilic Treatments of Nonwovens (High-solids WEKO process).

| Example # | Surfactant | Ratio | Viscosity (cp) @ 20 sec$^{-1}$ 25 C | 47 C | Application Temp. (C) | Add-On (Wt. %) | EDANA-Fluid Strike-Through Time (sec.) Cycle 1 | 2 | 3 | 4 | 5 |
|---|---|---|---|---|---|---|---|---|---|---|---|
| 1 | Ahcovel/Glucopon | 10:1 | <12 | | 25 | 0.3 | 8.7 | 8.3 | 9.6 | 10.8 | 11.8 |
| 2 | Ahcovel/Glucopon | 10:1 | <12 | | 25 | 0.6 | 8.8 | 9.3 | 10.7 | 10.4 | 12.6 |
| 3 | Ahcovel/Glucopon | 10:1 | <12 | | 25 | 0.9 | 7.8 | 7.7 | 8.1 | 8.5 | 9.1 |
| 4 | Ahcovel/Glucopon | 15:1 | 14 | | 25 | 0.3 | 8.4 | 8.2 | 9.1 | 9.8 | 10.5 |
| 5 | Ahcovel/Glucopon | 15:1 | 14 | | 25 | 0.5 | 8.6 | 7.9 | 8.1 | 8.3 | 8.5 |
| 6 | Ahcovel/Glucopon | 15:1 | 14 | | 25 | 0.9 | 7.8 | 8.5 | 8.4 | 8.9 | 10.2 |
| 7 | Ahcovel/Glucopon | 20:1 | 40 | | 25 | 0.3 | 9.3 | 10 | 12.1 | 13.9 | 12.1 |
| 8 | Ahcovel/Glucopon | 20:1 | 40 | | 25 | 0.5 | 8.7 | 8.9 | 9.2 | 8.6 | 10.8 |
| 9 | Ahcovel/Glucopon | 20:1 | 40 | | 25 | 0.9 | 7.9 | 9.1 | 8.6 | 10.2 | 10.1 |
| 10 | Ahcovel/Glucopon/SF 19 | 20:1:1 | 80 | | 25 | 0.3 | 7.8 | 7.9 | 7.7 | 8.1 | 9.1 |
| 11 | Ahcovel/Glucopon/SF 19 | 20:1:1 | 80 | | 25 | 0.6 | 7.7 | 8.1 | 8.4 | 7.9 | 9.2 |
| 12 | Ahcovel/Glucopon/SF 19 | 20:1:1 | 80 | | 25 | 0.9 | 7.7 | 7.6 | 8.3 | 8.3 | 8.7 |
| 13 | Ahcovel/Glucopon/SF 19 | 10:1:1 | 28 | | 25 | 0.3 | 7.1 | 8.6 | 8.5 | 8.2 | 9.7 |
| 14 | Ahcovel/Glucopon/SF 19 | 10:1:1 | 28 | | 25 | 0.6 | 7.2 | 7.5 | 8.3 | 8.9 | 10.2 |
| 15 | Ahcovel/Glucopon/SF 19 | 10:1:1 | 28 | | 25 | 0.9 | 6.9 | 7.1 | 7.9 | 7.3 | 9.3 |
| 28 | Ahcovel | 1 | 1103 | 150 | 47 | 0.3 | 7.5 | 7.8 | 8.8 | 8.9 | 11.5 |
| 29 | Ahcovel | 1 | 1103 | 150 | 47 | 0.6 | 7.1 | 7.1 | 7.2 | 9.2 | 10.5 |
| 30 | Ahcovel | 1 | 1103 | 150 | 47 | 0.9 | 7.2 | 7.6 | 7.4 | 8.5 | 9.6 |
| 31 | Glucopon 220 UP | 1 | <12 | | 25 | 0.3 | 7.5 | 8.9 | 11.5 | 16.5 | 17.6 |
| 32 | Glucopon 220 UP | 1 | <12 | | 25 | 0.6 | 7.6 | 9.2 | 10.9 | 11.8 | 12.9 |
| 33 | Glucopon 220 UP | 1 | <12 | | 25 | 0.9 | 7.1 | 8.2 | 9.7 | 11.8 | 12.3 |
| 34 | Triton X-102 | 1 | 120 | 23 | 47 | | 7.6 | 11.5 | 14.9 | 17.5 | 16.9 |
| 35 | Triton X-102 | 1 | 120 | 23 | 47 | | 7.5 | 9.3 | 15.6 | 16.7 | 14.9 |
| 36 | Triton X-102 | 1 | 120 | 23 | 47 | | 7.1 | 9.8 | 13.7 | 18.9 | 17.6 |

Example 77

A sheet of a metallocene polyolefin foam (OPCELL LC31 foam from Sentinel Products Corp., Hyannis, Mass.) was cut to a thickness of 0.25 inch (ca. 0.6 cm). Foam samples were saturated with 1% solution of Ahcovel/Glucopon blended at 15:1 weight ratio and with 1% Triton X-102. The treated Example 79

The fabric employed in example 79 was a 2.5 osy (about 85 gsm) spunbond nonwoven fabric in which the fibers were side-by-side bicomponent fibers. The components, which were present in approximately equal amounts, consisted of polyethylene and polypropylene. The fabric was cut into 8 inches by 10 inches. The fabric specimen was immersed for about 30 seconds in a solution composed of 3 wt % Ahcovel/Glucopon at 3:1 ratio. The measured WPU, as herein described, was about 200%, thus yielding a surfactant treatment of the fabric at about 6 wt % add-on level. The treated fabric was tested for water wettability by placing 10 water drops (ca. 0.1 ml) across the width of the fabric. All 10 water drops absorbed instantly into the fabric indicating that the treatment applied imparted a uniform and a highly hydrophilic character to the fabric. Control untreated fabric subjected to the same water drop test showed that none of the 10 drops of water penetrated or absorbed into the nonwoven fabric.

Example 80

The fabric employed in example 80 was a 100 gsm bonded carded web (BCW) in which the fibers were 3 dpf and made of bicomponent polyethylene/polypropylene in a sheath/core configuration, respectively. The fabric was cut into 8 inches by 10 inches. The fabric specimen was immersed for about 30 seconds in a solution composed of 3 wt % Ahcovel/Glucopon at 3:1 ratio. The measured WPU, as herein described, was about 100%, thus yielding a surfactant treatment of the fabric at about 3 wt % add-on level. The treated fabric was tested for water wettability by placing 10 water drops (ca. 0.1 ml) across the width of the fabric. All 10 water drops absorbed instantly into the fabric indicating that the treatment applied imparted a uniform and a highly hydrophilic character to the BCW fabric. Control untreated fabric (free of spin finish) subjected to the same water drop test showed that none of the 10 drops of water penetrated or absorbed into the nonwoven fabric.

Examples 81–88

Surfactant formulations were prepared by combining a first surfactant, Ahcovel Base N-62, with a second surfactant, Masil SF-19, at various ratios ranging from 100% Ahcovel Base N-62 to 100% Masil SF-19. In each case, the surfactants were combined in an aqueous emulsion containing 20% by weight total surfactant solids and 80% by weight water. The emulsions were homogenized by mixing at an elevated temperature of 130° F. The resulting surfactant combinations were then applied at various levels to as a polypropylene spunbond fabric having as a basis weight of 0.6 osy as described above.

The following Table 8 shows the ratio of Ahcovel Base N-62 to Masil SF-19 in each surfactant combination, and the amount applied relative to the basis weight of the nonwoven web.

TABLE 8

| Example # | Ahcovel Base N-62 parts by weight | Masil SF-19 parts by weight | Amount Applied To Nonwoven Web |
|---|---|---|---|
| 81 | 100 | 0 | 0.3% |
| 82 | 0 | 100 | 0.3% |
| 83 | 75 | 25 | 0.3% |
| 84 | 83.3 | 16.7 | 0.3% |
| 85 | 90 | 10 | 0.3% |
| 86 | 75 | 25 | 0.6% |
| 87 | 75 | 25 | 0.9% |
| 88 | 75 | 25 | 1.5% |

The treated nonwoven web samples were measured for liquid strike-through using the test identified as EDANA 150.1-90, described above. The measurements were taken after the nonwoven webs were exposed to 1–5 wash cycles, wherein the treated webs were washed and dried according to the procedures described above.

Figure 3:
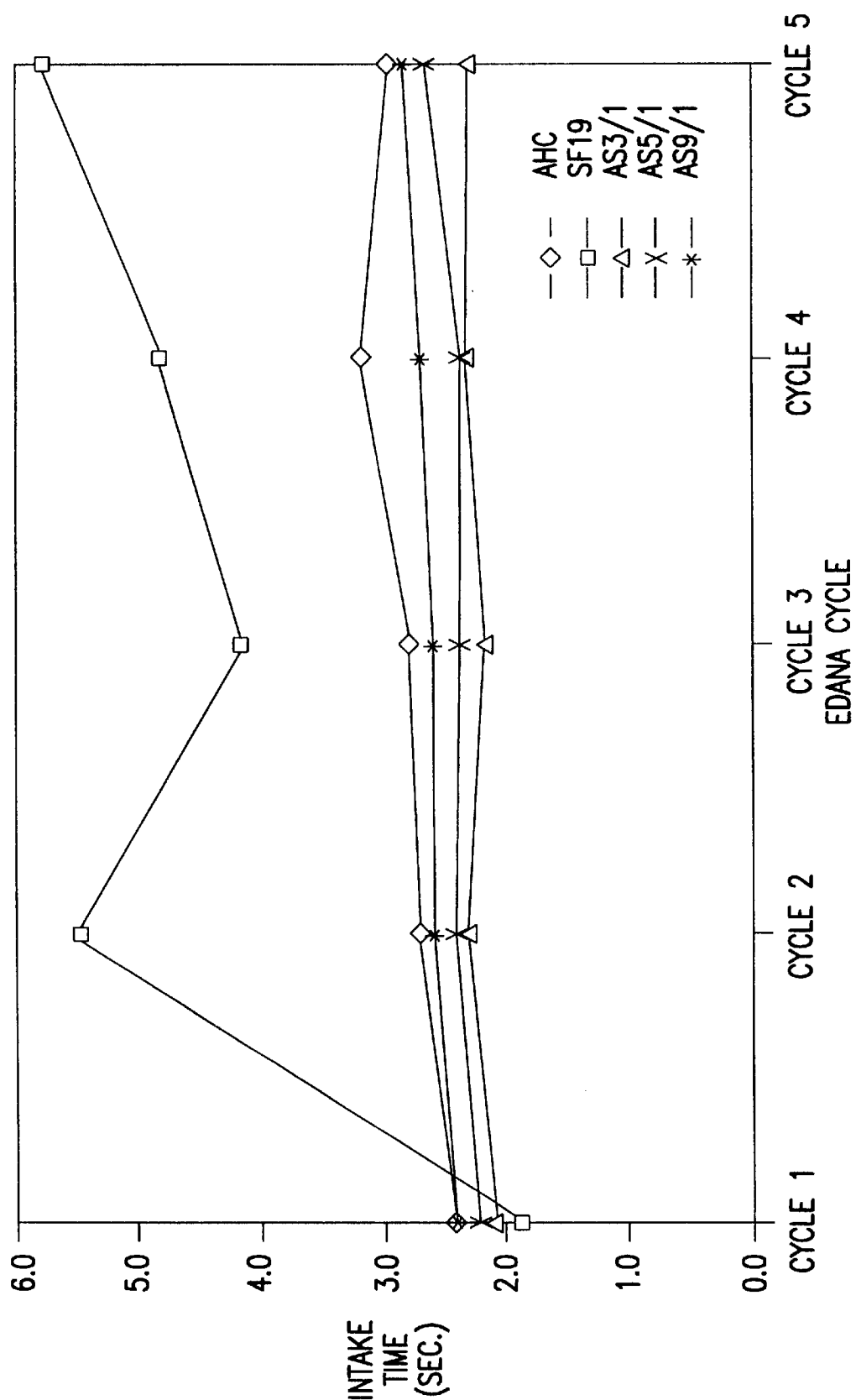
FIG. 3 is a plot showing intake time versus cycle for nonwovens treated with different ratios of a surfactant combination of the invention, as discussed in Examples 81–85.

Table 9 (below) shows the intake time of the liners treated with the various surfactant combinations at as a constant coating of 0.3% by weight, after 1–5 wash cycles. The results of this comparison are plotted in FIG. 3.

TABLE 9

| | | Intake Time, Seconds | | | | |
|---|---|---|---|---|---|---|
| Example # | Ratio of Ahcovel to Masil SF-19 | Cycle 1 | Cycle 2 | Cycle 3 | Cycle 4 | Cycle 5 |
| 81 | 100:0 | 2.4 | 2.7 | 2.8 | 3.2 | 3.0 |
| 82 | 0:100 | 1.9 | 5.5 | 4.2 | 4.8 | 5.8 |
| 83 | 75:25 | 2.1 | 2.3 | 2.2 | 2.3 | 2.3 |
| 84 | 83.3:16.7 | 2.2 | 2.4 | 2.4 | 2.4 | 2.7 |
| 85 | 90:10 | 2.4 | 2.6 | 2.6 | 2.7 | 2.9 |

As shown above, and in FIG. 3, the samples treated with combined surfacants had lower fluid intake times after 2–5 wash cycles than the samples treated with pure Ahcovel Base N-62 or pure Masil SF-19. This indicates that samples treatment with the surfactant combinations have improved wettability (i.e., lower intake times) and improved durability (ability to withstand repeated washing and drying). The lowest fluid intake after repeated wash cycles consistently occurred for samples treated with the combination of 75 parts by weight Ahcovel per 25 parts by weight Masil SF-19.

Figure 4:
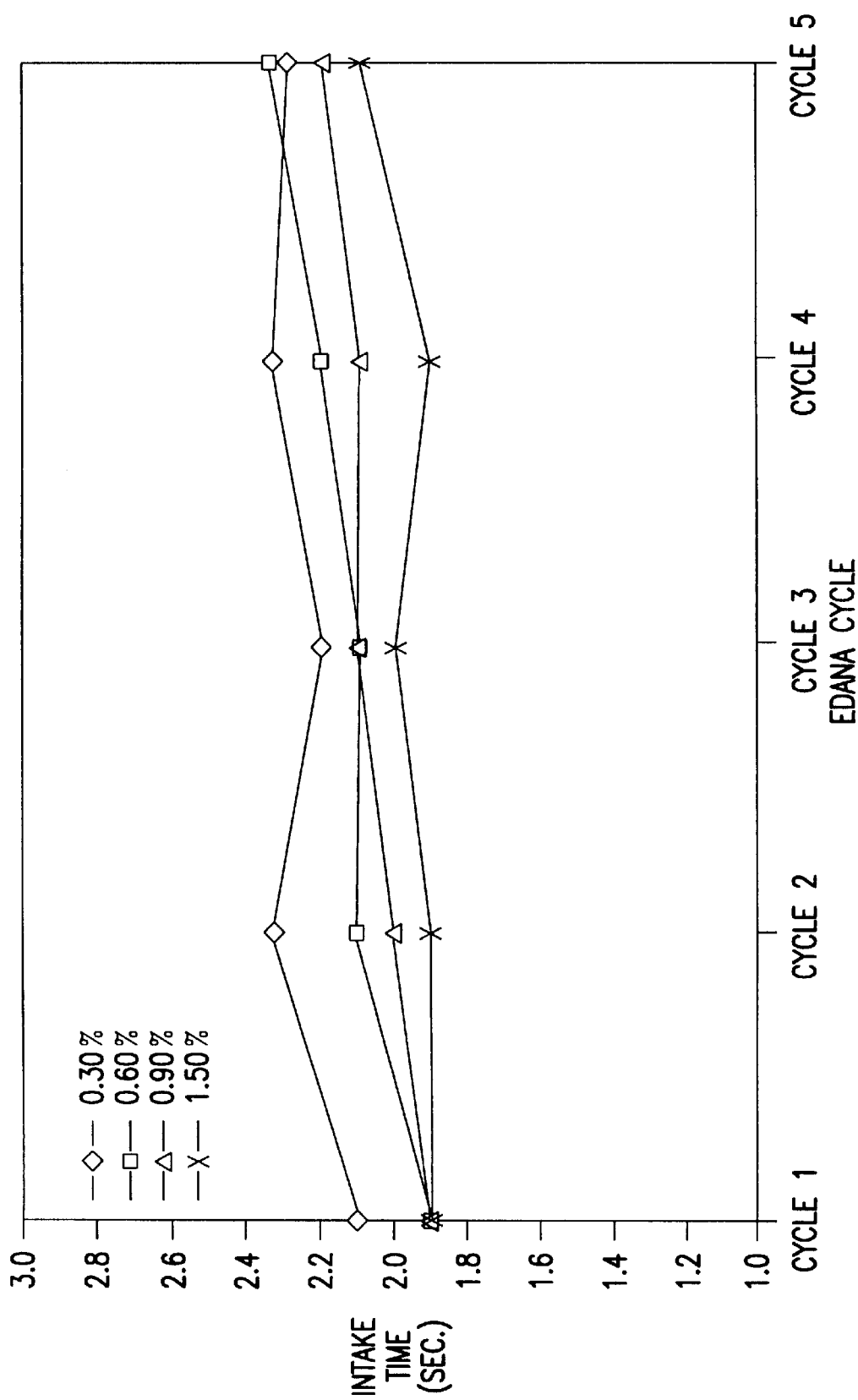
FIG. 4 is a plot showing intake time versus cycle for nonwovens treated with different levels of a surfactant combination of the invention, as discussed in Examples 83 and 86–88.

Table 10 (below) shows the intake time of the liners treated with various coating weights of the preferred combined surfactant having 75 parts by weight Ahcovel N-62 per 25 parts by weight Masil SF-19, after 1–5 wash cycles. The results of this comparison are plotted in FIG. 4.

TABLE 10

| | Coating Weight of | Intake Time, Seconds | | | | |
|---|---|---|---|---|---|---|
| Example # | Preferred Combined Surfactant | Cycle 1 | Cycle 2 | Cycle 3 | Cycle 4 | Cycle 5 |
| 83 | 0.3% | 2.1 | 2.3 | 2.2 | 2.3 | 2.3 |
| 86 | 0.6% | 1.9 | 2.1 | 2.1 | 2.2 | 2.3 |
| 87 | 0.9% | 1.9 | 2.0 | 2.1 | 2.1 | 2.2 |
| 88 | 1.5% | 1.9 | 1.9 | 2.0 | 1.9 | 2.1 |

As shown above, and in FIG. 4, the intake time improved only slightly as the coating level was raised from 0.3% to 1.5% of the basis weight of the nonwoven web. Thus, coating weights of less than 0.5% (e.g., 0.3%) yield excellent results in terms of low fluid intake times and long durabilities.

Thus, in accordance with the invention, there has been provided an improved treatment process and resulting treated nonwovens that provides the benefits described above. While the invention has been illustrated by specific embodiments, it is not limited thereto and is intended to cover all equivalents as come within the broad scope of the claims.

I claim:

1. A treatment composition for imparting durability and wettability to a substrate, comprising first and second surfactants in combination;

the first surfactant including an ethoxylated hydrogenated fatty oil and a compound selected from the group consisting of monosaccharides, monosaccharide derivatives, polysaccharides, polysaccharide derivatives, and combinations thereof;

the second surfactant including an organosilicon compound.

2. The treatment composition of claim 1, wherein the first and second surfactants are combined in an aqueous emulsion.

3. The treatment composition of claim 1, wherein the first surfactant comprises ethoxylated hydrogenated castor oil.

4. The treatment composition of claim 1, wherein the first surfactant comprises a compound selected from the group consisting of monosaccharides, monosaccharide derivatives and combinations thereof.

5. The treatment composition of claim 4, wherein the first surfactant comprises sorbitan monooleate.

6. The treatment composition of claim 1, wherein the first surfactant comprises ethoxylated hydrogenated castor oil and sorbitan monooleate.

7. The treatment composition of claim 1, wherein the second surfactant comprises an alkoxylated polysiloxane.

8. The treatment composition of claim 7, wherein the second surfactant comprises an alkoxylated trisiloxane.

9. The treatment composition of claim 1, wherein the first and second surfactants are present at a weight ratio of about 50–99.5 parts by weight first surfactant to about 0.5–50 parts by weight second surfactant.

10. The treatment composition of claim 1, wherein the first and second surfactants are present at a weight ratio of about 65–95 parts by weight first surfactant and about 5–35 parts by weight second surfactant.

11. The treatment composition of claim 1, wherein the first and second surfactants are present at a weight ratio of about 70–85 parts by weight first surfactant and about 15–30 parts by weight second surfactant.

12. The treatment composition of claim 1, further comprising a biofunctional additive.

13. The treatment composition of claim 12, wherein the biofunctional additive comprises a skin wellness additive.

14. A substrate treated with a composition comprising first and second surfactants;

the first surfactant including an ethoxylated hydrogenated fatty oil and a compound selected from the group consisting of monosaccharides, monosaccharide derivatives, polysaccharides, polysaccharide derivatives, and combinations thereof;

the second surfactant including an organosilicon compound.

15. The treated substrate of claim 14, wherein the substrate comprises a nonwoven web.

16. The treated substrate of claim 15, wherein the nonwoven web comprises a spunbond web.

17. The treated substrate of claim 15, wherein the nonwoven web comprises a meltblown web.

18. The treated nonwoven fabric of claim 15, wherein said fabric having an intake time of less than 3.0 seconds, tested according to EDANA 150.1-90, after four wash cycles.

19. The treated nonwoven fabric of claim 18, wherein the intake time remains less than 3.0 seconds after five wash cycles.

20. The treated nonwoven fabric of claim 18, wherein the nonwoven fabric comprises a spunbond web.

21. The treated nonwoven fabric of claim 20, wherein the spunbond web comprises polypropylene.

22. The treated nonwoven fabric of claim 18, treated with less than 0.5% by weight of a surfactant combination.

23. The treated nonwoven fabric of claim 18, wherein the intake time is less than 2.8 seconds after five wash cycles.

24. The treated nonwoven fabric of claim 18, wherein the intake time is less than 2.6 seconds after five wash cycles.

25. The treated nonwoven fabric of claim 18, wherein the intake time is less than 2.4 seconds after five wash cycles.

26. The treated substrate of claim 14, wherein the substrate comprises a multilayer laminate.

27. The treated substrate of claim 14, wherein the first surfactant comprises a compound selected from the group consisting of monosaccharides, monosaccharide derivatives, and combinations thereof.

28. The treated substrate of claim 27, wherein the second surfactant comprises an alkoxylated polysiloxane.

29. The treated substrate of claim 14, wherein the first surfactant comprises ethoxylated hydrogenated castor oil.

30. The treated substrate of claim 14, wherein the first surfactant comprises sorbitan monooleate.

31. The treated substrate of claim 14, wherein the second surfactant comprises an alkoxylated polysiloxane.

32. The treated substrate of claim 14, wherein the surfactant composition is applied at a level of about 0.1–1.5% by weight surfactant solids relative to the basis weight of the substrate.

33. The treated substrate of claim 14, wherein the surfactant composition is applied at a level of about 0.1–1.0% by weight surfactant solids relative to the basis weight of the substrate.

34. The treated substrate of claim 14, wherein the surfactant composition is applied at a level of about 0.1–0.5% by weight surfactant solids relative to the basis weight of the substrate.

35. The treated substrate of claim 14, wherein the composition further comprises a biofunctional additive.

36. The treated substrate of claim 35, wherein the biofunctional additive comprises a skin wellness additive.

* * * * *